United States Patent [19]

Muchel et al.

[11] 4,249,802
[45] Feb. 10, 1981

[54] OPHTHALMOLOGICAL INSTRUMENT

[75] Inventors: Franz Muchel, Königsbronn; Gunther Sümmerer, Oberkochen, both of Fed. Rep. of Germany

[73] Assignee: Carl Zeiss-Stiftung, Oberkochen, Fed. Rep. of Germany

[21] Appl. No.: 942,217

[22] Filed: Sep. 14, 1978

[30] Foreign Application Priority Data

Sep. 17, 1977 [DE] Fed. Rep. of Germany ....... 2741992

[51] Int. Cl.³ ............................................... A61B 3/14
[52] U.S. Cl. ........................................... 351/7; 351/16
[58] Field of Search ....................... 354/62; 351/7, 16

[56] References Cited

U.S. PATENT DOCUMENTS

| 887,032 | 5/1908 | De Zeng | 351/16 X |
| 3,591,262 | 7/1971 | Gambs | 351/16 X |
| 4,149,787 | 4/1979 | Kobayashi et al. | 351/7 X |

FOREIGN PATENT DOCUMENTS 2655859 12/1976 Fed. Rep. of Germany .............. 351/7
1129603 9/1956 France ......................................... 351/7

OTHER PUBLICATIONS

J. M. Parel et al., "Simultaneous . . . Camera", *Am. J. Opth.*, vol. 85, pp. 230–236, 2/1978.

Primary Examiner—Paul A. Sacher
Attorney, Agent, or Firm—Stonebraker, Shepard & Stephens

[57] ABSTRACT

An ophthalmological instrument having optical elements providing an examination light beam path and an illumination light beam path. The optical elements include an objective for producing an inverted magnified flattened image of the fundus of the eye, and further elements for focusing this image at infinity and projecting it selectively either into an observation tube or into a camera or other documentation device where a record of the image may be made. The illumination beam path includes a source of light and means of projecting this light, via a perforated mirror, into the pupil of the patient.

8 Claims, 1 Drawing Figure

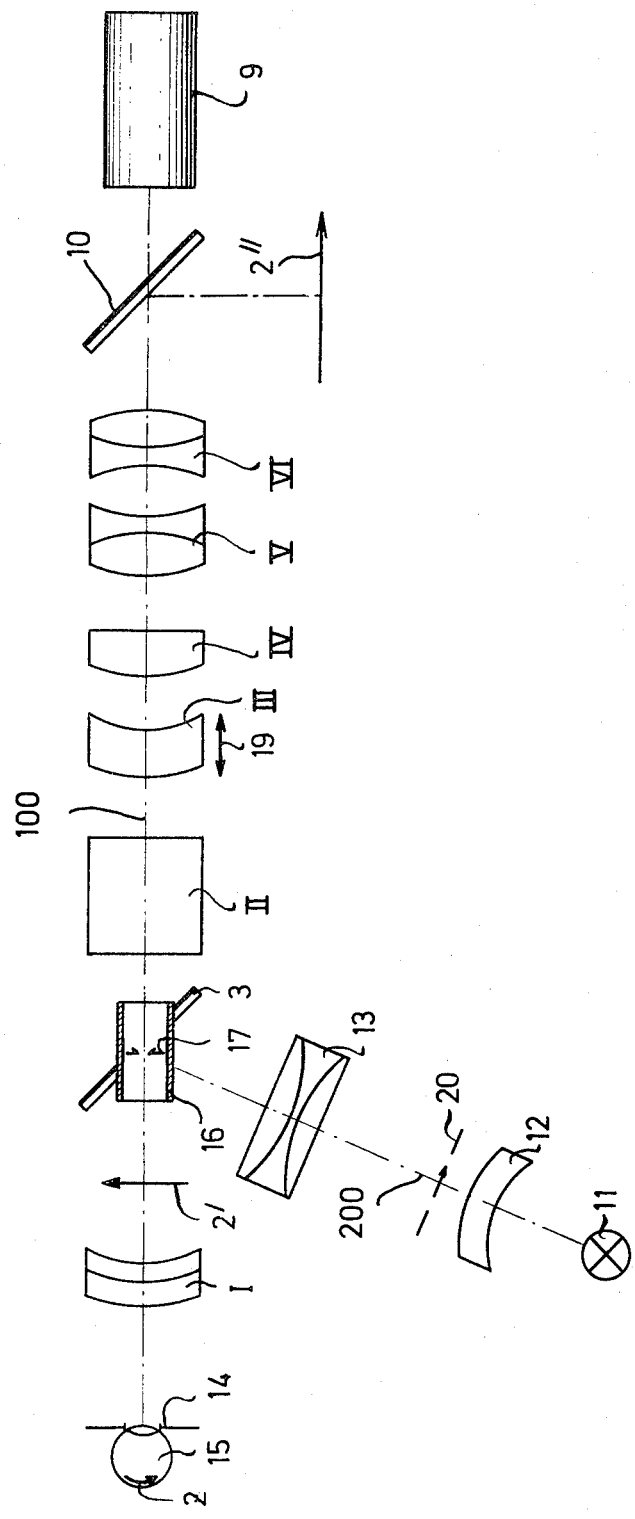

OPHTHALMOLOGICAL INSTRUMENT

This invention relates to an ophthalmological instrument for examining and photographing the fundus or retina of the eye, the instrument having an illuminating beam path and an observation beam path.

Ophthalmological instruments for examining the fundus of the eye are known in various embodiments, ranging from small instruments for ophthalmoscopy with erect and inverted image (so-called funduscope or ophthalmoscope) up to the fundus camera with documentation possibilities. These, at greater or lesser expense, satisfy special requirements in connection with the examination of the fundus of the eye.

The known small instruments which permit a rapid inspection of the fundus due to their low weight and ease in handling are limited to brief visual inspections of the fundus or retina, despite the fact that in part they are equipped with comfortable and diversified accessories. Since they are developed as manual instruments, they lack, in particular, the possibility of a quiescent or stationary position of the image, and the possibility of documentation, that is, taking photographs or making other permanent records of the appearance of the retina. Column-type instruments with possibility of documentation are also known in various embodiments and under various names. They are generally characterized by high optical requirements and a large size, and often a rather large cost.

The object of the present invention is to provide an ophthalmological instrument for the examination and photographing of the fundus of the eye by means of which all known standard methods of observing and documenting the fundus can be carried out in routine operation with extremely simple handling thereof, and in a manner which, due to simple operation and compactness, assures a proper diagnosis by a substantially larger group of users as a result of the photographing or other documentation of what is seen.

Another object is to expand the possibilities of diagnosis by the establishing of fluorescence angiograms and by stereoscopic observation of the fundus via a splitting of the beam. Furthermore, the optical equipment of the instrument is of such a nature that it can be arranged in a slender, short basic body.

SUMMARY OF THE INVENTION

The above mentioned objects are achieved in accordance with the invention in the manner that, within the path of the observation beam, in the direction from the eye of the patient to the observation tube, there are arranged an objective for producing an inverted magnified flattened image of the fundus of the eye, a perforated mirror, a reflection prism, a lens group for focusing the first flattened image at infinity, and another lens group for producing an erect image of the fundus. Also a collector and a lens group are provided in the path of the illumination beam for imaging a source of light via the said perforated mirror into the pupil of the patient.

For compensation for ametropia, the group of lenses provided for focusing at infinity is preferably axially displaceable. By such internal focusing, assurance is had that the structural length of the instrument does not change during handling. By means of a swivel mirror which is arranged at the locus of the vertical image of the fundus, the image can be deflected, as desired, to an observation tube or to a documentation device, for instance a camera.

In order to make certain that no light from the illumination beam path disturbs the observation beam path, an aperture stop is arranged in a small tube along the axis of the observation beam in the perforated mirror.

As a source of light to be imaged in the pupil of the patient, there can be employed, as desired, either the filament of an incandescent bulb, or the plasma of a flash lamp, or the exit surface of a light pipe.

Marks of any desired kind (e.g., scale graduations or other reference marks) can be arranged behind the collector in the illumination beam path, which marks appear on the fundus.

BRIEF DESCRIPTION OF THE DRAWING

The single view is a diagrammatic showing of the optical structure of the instrument in accordance with a preferred embodiment of the invention.

DESCRIPTION OF THE PREFERRED EMBODIMENT

In the path of the observation beam 100 a main objective I is arranged behind the eye 15 of the patient having the retinal fundus 2 and the pupil 14. In the case of an emmetropic eye of the patient the retina 2 is focused at the focal point of the main objective. This image 2' is flat and inverted.

Instead of the central diaphragm customary in known instruments which is provided in the path of the illumination beam, the aperture stop 17 is, in the case of the instrument of the present invention, arranged in a small tube 16 along the axis of the observation path in the perforated mirror 3. The tube 16 serves to protect against reflections. By means of the reflecting prism II, shown in plan view, the beam can be deviated or reflected in a conventional manner not illustrated, to accommodate it to an optimal shape of housing.

The lens group III receives the fundus image 2' and focuses it on infinity. The lens group IV, V and VI produce a real image 2'' of the fundus, which can alternatively be observed by means of a swivel mirror 10 via a tube 9 or be fed to suitable optical devices (e.g., a camera) for documentation. The lens III is axially displaceable in the direction 19 in order to compensate for ametropia. The lens groups I, III, IV, V, and VI can also be used decentered without impairing the quality of the imaging. This is done, for instance, if, for purposes of stereoscopic observation of the retina, Abbe half-stops are arranged in the exit pupils of the oculars. An image of the pupil 14 is produced approximately at the object-side focal point of the lens combination IV, V, VI, so that even for ametropic eyes of the patient the field stop or the photographic format is always filled by the image of the fundus.

In the illumination beam path or beam 200, the source of light, which may be developed as a filament of an incandescent bulb, or as plasma of a flash lamp, or as an exit surface of a light pipe, is designated 11. It is imaged by the collector lens 12 and the lens group 13 onto the perforated mirror 3 and from there, via the main objective 1, into the pupil 14 of the patient. Marks or the like can be arranged in the plane 20, and then appear on the fundus.

The constructional details of the various optical components are subject to some variation within the skill of the art, once the nature and purpose and arrangement of the components are understood from the present disclosure. Constructional details which are particularly satisfactory are those indicated in the following table, where each lens component in the observation beam path is identified by the Roman numeral in the left hand column, corresponding to the respective Roman numeral used in the foregoing description and in the drawing. The other data in the table are given in the form commonly used in lens patents and will be readily understood by those familiar with lens patent usage.

The radii of the respective surfaces are indicated by R with a subscript identifying the surface as numbered consecutively from front to rear. Radii are understood to be positive unless preceded by a minus sign. Positive radii represent surfaces convex toward the front, that is, toward the eye of the patient being examined. Negative radii represent surfaces concave toward the front. Thicknesses are indicated by D with a subscript identifying the particular element, numbered consecutively from front to rear. Air spaces are indicated by S with a subscript identifying the space, again numbered from front to rear, the first space being the free space or working space between the front lens and the eye of the patient. All linear dimensions are expressed in millimeters. The index of refraction of each element (identified by appropriate subscript) is given with respect to a convenient reference line commonly referred to in the catalogs of manufacturers of optical glass; for example, the yellow d-line of the helium spectrum, with a wavelength of 5876 Angstrom units. The index of dispersion or Abbe number is also given in the table. It should be understood that all numerical data are subject to a reasonable tolerance of plus or minus five per cent, or more where appropriate.

| Lens | Radius (R) | Thickness (D) | Air space (S) | Index of refraction $n_d$ | Abbe number V |
|---|---|---|---|---|---|
|  |  |  | $S_1=40$ |  |  |
|  | $R_1=13.050$ |  |  |  |  |
|  |  | $D_1=7.0$ |  | $n_{d1}=1.522489$ | $v_1=59.48$ |
| I | $R_2=31.623$ |  |  |  |  |
|  |  | $D_2=4.8$ |  | $n_{d2}=1.522489$ | $v_2=59.48$ |
|  | $R_3=88.486$ |  |  |  |  |
|  |  |  | $S_2=99.5$ |  |  |
|  | $R_4=$ Plane |  |  |  |  |
| II |  | $D_3=43.0$ |  | $n_{d3}=1.51680$ | $v_3=64.17$ |
|  | $R_5=$ Plane |  |  |  |  |
|  |  |  | $S_3=17.0$ |  |  |
|  | $R_6=57.461$ |  |  |  |  |
| III |  | $D_4=3.5$ |  | $n_{d4}=1.76180$ | $v_4=26.95$ |
|  | $R_7=139.24$ |  |  |  |  |
|  |  |  | $S_4=15.3$ |  |  |
|  | $R_8=143.30$ |  |  |  |  |
| IV |  | $D_5=3.5$ |  | $n_{d5}=1.76180$ | $v_5=26.95$ |
|  | $R_9=$ Plane |  |  |  |  |
|  |  |  | $S_5=13.8$ |  |  |
|  | $R_{10}=17.783$ |  |  |  |  |
|  |  | $D_6=8.5$ |  | $n_{d6}=1.51680$ | $v_6=64.17$ |
| V | $R_{11}=-25.119$ |  |  |  |  |
|  |  | $D_7=3.1$ |  | $n_{d7}=1.784701$ | $v_7=26.08$ |
|  | $R_{12}=27.582$ |  |  |  |  |
|  |  |  | $S_6=5.8$ |  |  |
|  | $R_{13}=-19.81$ |  |  |  |  |
|  |  | $D_8=2.0$ |  | $n_{d8}=1.522489$ | $v_8=59.48$ |
| VI | $R_{14}=20.684$ |  |  |  |  |
|  |  | $D_9=8.5$ |  | $n_{d9}=1.582670$ | $v_9=46.47$ |
|  | $R_{15}=-25.3$ |  |  |  |  |
|  |  |  | $S_7=130.3$ |  |  |

Although certain lens groups have been mentioned above, the use of the word "group" is not meant to imply the presence of more than a single element in the "group" or component. It will be seen from the foregoing table that in the preferred construction, groups or components III and IV, for example, each consist of only a single element, while two elements are used in each of groups or components I, V, and VI.

The advantages obtained with the invention consist, in particular, in the fact that the instrument can be developed with a slender, short basic body, that it operates with a so-called free working distance of 40 mm, and that it can thus also be used by semi-skilled persons. It is also advantageous for its use that the imaging optics are so designated that a conventional angle of view of 30 degrees is obtained, so that comparative examinations which have been carried out for many years can be continued with this instrument and customary impressions and dimensions are not disturbed. The instrument is intended for the documentation of the findings for standard methods of black-and-white and color photography, instant photography, and fluorescence angiography. It takes but a moment to shift the swivel mirror 10 to a position to deflect the observation beam to fall on the film plane 2" of a conventional camera. The instrument permits the use of filters and additionally enlarging objectives, as well as the possibility of rapid sequence of flashes and mirroring-in of data. From the standpoint of expense, it is excellently suited for clinical routine, and for the practice of the ophthalmologist, and for preventive medicine.

As a result of the possibility of stereoscopic observation of the fundus, the examination of, for instance, glaucomatous excavation of the papilla of the optic nerve or vertification of the cause of the formation of prominence is facilitated.

What is claimed is:

1. Ophthalmological instrument for examining and photographing the fundus of the eye, said instrument comprising means forming an illuminating beam path and an observation beam path, said observation beam path having, successively in a direction from the eye (15) of a patient to be examined toward the eye of a person making the examination, an objective (I) for producing an inverted magnified flattened image (2') of the fundus (2) of the eye being examined, a perforated mirror (3) through a perforation in which the observation beam path extends, a reflecting prism (II), a lens group (III) for focusing said image (2') at infinity, further lens groups (IV, V, VI) for producing an erect image (2") of the fundus of the eye, and an observation tube (9), said illumination beam path including a source of light (11), a collector (12), and a lens group (13) for focusing said source of light into the pupil (14) of the eye of the patient via said perforated mirror (3), at said objective, prism, and lens groups in said observation beam path having characteristics substantially within a tolerance range of plus or minus five percent of the numerical values indicated in the following table, the respective symbols having the meanings explained in the accompanying specification:

| Lens | Radius (R) | Thickness (D) | Air space (S) | Index of refraction $n_d$ | Abbe number V |
|---|---|---|---|---|---|
|  |  |  | $S_1=40$ |  |  |
|  | $R_1=13.050$ |  |  |  |  |
|  |  | $D_1=7.0$ |  | $n_{d1}=1.522489$ | $v_1=59.48$ |
| I | $R_2=31.623$ |  |  |  |  |
|  |  | $D_2=4.8$ |  | $n_{d2}=1.522489$ | $v_2=59.48$ |
|  | $R_3=88.486$ |  |  |  |  |
|  |  |  | $S_2=99.5$ |  |  |
|  | $R_4=$ Plane |  |  |  |  |

-continued

| Lens | Radius (R) | Thickness (D) | Air space (S) | Index of refraction $n_d$ | Abbe number $\nu$ |
|---|---|---|---|---|---|
| II | | $D_3 = 43.0$ | | $n_{d3} = 1.51680$ | $\nu_3 = 64.17$ |
| | $R_5 = $ Plane | | $S_3 = 17.0$ | | |
| | $R_6 = 57.461$ | | | | |
| III | | $D_4 = 3.5$ | | $n_{d4} = 1.76180$ | $\nu_4 = 26.95$ |
| | $R_7 = 139.24$ | | $S_4 = 15.3$ | | |
| | $R_8 = 143.30$ | | | | |
| IV | | $D_5 = 3.5$ | | $n_{d5} = 1.76180$ | $\nu_5 = 26.95$ |
| | $R_9 = $ Plane | | $S_5 = 13.8$ | | |
| | $R_{10} = 17.783$ | | | | |
| | | $D_6 = 8.5$ | | $n_{d6} = 1.51680$ | $\nu_6 = 64.17$ |
| V | $R_{11} = -25.119$ | | | | |
| | | $D_7 = 3.1$ | | $n_{d7} = 1.784701$ | $\nu_7 = 26.08$ |
| | $R_{12} = 27.582$ | | $S_6 = 5.8$ | | |
| | $R_{13} = -19.81$ | | | | |
| | | $D_8 = 2.0$ | | $n_{d8} = 1.522489$ | $\nu_8 = 59.48$ |
| VI | $R_{14} = 20.684$ | | | | |
| | | $D_9 = 8.5$ | | $n_{d9} = 1.582670$ | $\nu_9 = 46.47$ |
| | $R_{15} = -25.3$ | | | | |
| | | | $S_7 = 130.3$ | | |

2. The invention defined in claim 1, wherein said lens group (III) for focusing said image at infinity is axially displaceable.

3. The invention defined in claim 1, further comprising a swivel mirror (10) arranged between the last lens group (VI) and the erect image (2″).

4. The invention defined in claim 1, further comprising a tube (16) aligned with said observation beam path and extending through said perforation in said perforated mirror, and an aperture stop (17) in said tube (16).

5. The invention defined in claim 1, wherein said source of light (11) is a filament of an incandescent bulb.

6. The invention defined in claim 1, wherein said source of light (11) is plasma of a flash lamp.

7. The invention defined in claim 1, wherein said source of light (11) is an exit surface of a light pipe.

8. The invention defined in claim 1, further comprising means in said illumination beam path for providing marks to be projected onto the fundus of the eye being examined.

* * * * *